United States Patent
Fry

[11] Patent Number: 5,843,101
[45] Date of Patent: Dec. 1, 1998

[54] DISPOSABLE CLIP FOR TEMPORARY VESSEL OCCULSION

[76] Inventor: William R. Fry, 605 Echolan St., Colorodo Springs, Colo. 80906

[21] Appl. No.: 850,060

[22] Filed: May 2, 1997

[51] Int. Cl.$^6$ .................................................. A61B 17/04
[52] U.S. Cl. ........................... 606/157; 606/151; 227/902
[58] Field of Search ..................... 606/142, 143, 606/151, 157; 227/902

[56] References Cited

U.S. PATENT DOCUMENTS

| | | | |
|---|---|---|---|
| 4,269,190 | 5/1981 | Behney | 606/157 |
| 4,822,348 | 4/1989 | Casey . | |
| 5,171,253 | 12/1992 | Klieman | 606/158 |
| 5,282,812 | 2/1994 | Suarez, Jr. | 606/158 |
| 5,304,183 | 4/1994 | Gourlay et al. | 606/142 |
| 5,306,283 | 4/1994 | Connors | 606/151 |

*Primary Examiner*—Gary Jackson
*Attorney, Agent, or Firm*—Gifford,Krass,Groh,Sprinkle,Patmore, Anderson & Citkowski

[57] ABSTRACT

A disposable clip which finds application in the temporary occlusion of blood vessels, bowels, ducts, and so forth, consumes a small volume within an operative field during use, and may be removed without the need for highly specialized tools. In terms of construction, a pair of substantially rigid, spaced-apart members are joined by way of a malleable hinge. Each member includes an inwardly oriented surface which oppose and face one another and outwardly oriented surfaces which face away from one another. A layer of compressible material is supported against the inwardly oriented surface of each member and, with an externally applied pressure exerted upon the outwardly oriented surfaces, the pair of rigid members are urged toward one another, thereby compressing and at least temporarily occluding the vessel between the layers of compressible material, with the malleable hinge maintaining the clip in this configuration until removal. Means are further provided enabling the members and layers of compressible material to separate from one another through the application of an externally applied removal force.

5 Claims, 1 Drawing Sheet

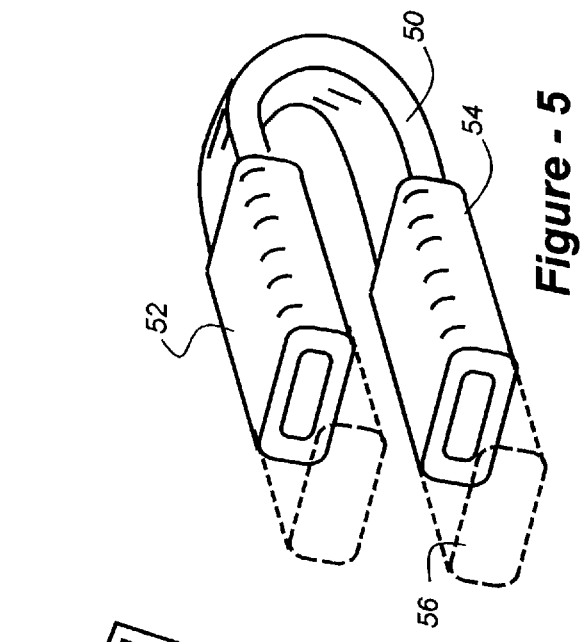
Figure - 5
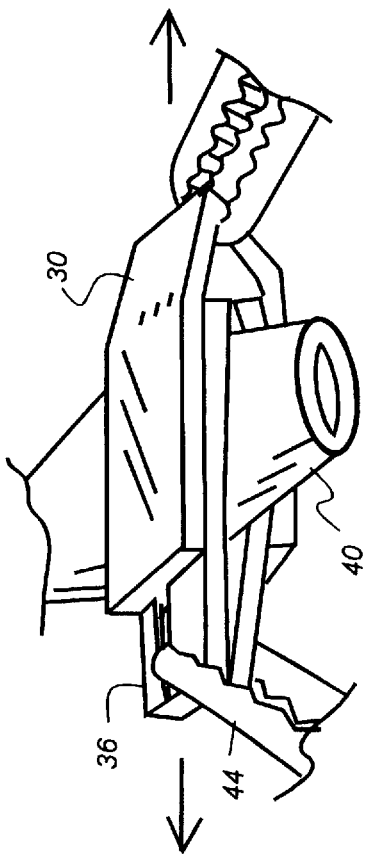
Figure - 3
Figure - 4
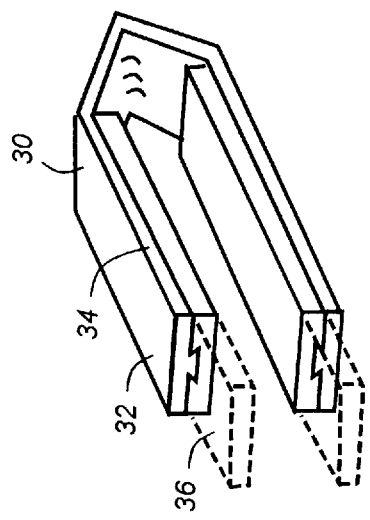
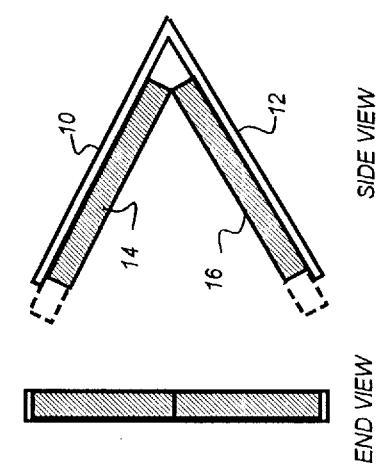
Figure - 1
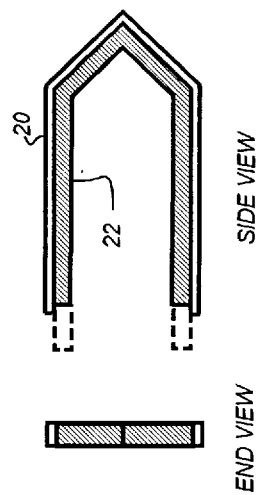
Figure - 2

DISPOSABLE CLIP FOR TEMPORARY VESSEL OCCULSION

FIELD OF THE INVENTION

This invention relates generally to surgical procedures, and, in particular, to a disposable clip which may be used to temporarily occlude blood vessels, intestinal tracts, bile ducts, and so forth, so as to keep an operative field dry and free of unnecessary surgical instrumentation.

BACKGROUND OF THE INVENTION

During vascular surgical procedures, there is a need for temporary vascular occlusion to facilitate operating in a dry field. Traditional techniques involve the use of modified hemostats, called vascular clamps, that attempt to co-apt the vessel with minimal harm to the vascular wall. The use of padded inserts has been added to help decrease any trauma to the vessel wall.

Unfortunately, one of the problems with traditional vascular clamps is that they hinder the operator in being able to access the operative field. This is because the vascular clamp handle often times must reside in the operative field. Many different shapes of clamps have been made to remove the clamp handle from the operative field. Success of these variations usually only work well in a limited number of applications. One such attempt is disclosed in U.S. Pat. No. 5,282,812 to Suarez, Jr., entitled CLAMP FOR VASCULAR SURGERY. According to this reference, a surgical clamp for the temporary occlusion of a blood vessel during a surgical procedure and forceps-like instruments cooperate for application and removal of the clamp. Although a useful system is disclosed, its versatility is somewhat undermined by the need for a specialized removal tool.

SUMMARY OF THE INVENTION

The present invention resides in a disposable clip for temporarily occluding a vessel. In addition to vascular vessels, the clip may be applied to bowel, ducts, and any other conduit which might benefit from temporary occlusion. A disposable clip according to the invention consumes a small volume within an operative field during use, and may be removed without the need for highly specialized tools.

In terms of construction, the clip comprises a pair of substantially rigid, spaced-apart members, each having first and second ends, the first ends of the two members being joined through a malleable hinge. Each member includes an inwardly oriented surface which oppose and face one another and outwardly oriented surfaces which face away from one another. A layer of compressible material is supported against the inwardly oriented surface of each member, with the distance between the inwardly oriented surfaces, including the layers of compressible material, being sufficient to at least partially surround the vessel destined for temporarily occlusion. With an externally applied pressure exerted upon the outwardly oriented surfaces, the pair of rigid members are urged toward one another, thereby compressing and at least temporarily occluding the vessel between the layers of compressible material, with the malleable hinge maintaining the clip in this configuration until removal.

Means are further provided enabling the members and layers of compressible material to separate from one another through the application of an externally applied removal force. In one embodiment, the members and layers of compressible material separate from one another through the action of a break-away bond therebetween. In an alternative embodiment, a track feature is provided between the inwardly oriented surfaces of each member and the layers of compressible material, enabling the members and layers of compressible material to be pulled in opposite directions to bring about their separation.

BRIEF DESCRIPTION OF THE DRAWINGS

FIG. 1 is a simplified, side-view drawing of a V-shaped clip according to the invention;

FIG. 2 is an alternative embodiment of the invention which, when viewed from the side, takes on more a U-shaped appearance as compared to the embodiment of FIG. 1;

FIG. 3 is a version of the invention wherein resilient pads slidingly engage with track features present on a metal portion of a clip;

FIG. 4 is a drawing which illustrates one way in which a clip according to the invention may be removed without the need for specialized tools; and FIG. 5 represents yet a further alternative embodiment of the invention wherein compressible sleeves are removably disposed over the ends of a metal clip.

DETAILED DESCRIPTION OF THE PREFERRED EMBODIMENT

This invention provides a clip having padded contact surfaces which may be used in vascular occlusion without crushing the vascular wall, a result which may occur with standard hemostatic clips. Once the clip has been applied, the applicator is removed, to achieve temporary vascular occlusion with a low-profile device, thereby minimizing the impact of the device on the operative field.

The device may have its greatest utility when dealing with temporary vascular occlusion below the knee and in relatively inaccessible areas such as the subclavian or visceral vessels.

Clips according to the invention may also be used for bowel occlusion in place of traditional bowel clamps. This would be helpful in two current situations, laparoscopic colon resection and initial control of traumatic enterotomies in patients suffering penetrating trauma. Placing the clips on the bowel would control bowel spillage, without injury to the bowel wall.

For laparoscopic use, the applier configuration would be of the type which fits through a trocar, enabling the clip to be opposed for entry into the abdomen, opened to put around the bowel, and then closed again to occlude the bowel lumen.

For the patient with enterotomies from penetrating trauma, or during iatrogenic enterotomy during dissection with unprepared bowel, the clips could be quickly applied to control spillage of bowel contents, but also bleeding without harm to the blood supply. This can be accomplished without cumbersome traditional clamps which routinely impede further dissection and/or exploration.

Reference is now made to the figures, in which FIG. 1 illustrates an embodiment of the invention wherein a pair of straight, preferably metal elements 10 and 12 connect at a point 12 forming a malleable hinge. The elements 10 and 12 include inwardly facing surfaces to which there is supported compressable pads 14 and 16, respectively, these pads being preferably constructed of silicone rubber, though other resilient materials may also serve this function. The metal used for the members 10 and 12 may be any suitable pure element such as aluminum, or metal alloy such as stainless steel, so long as the device may be sterilized and with the hinge portion 11 functioning adequately as described herein.

FIG. 2 illustrates a variation of the invention, wherein the metal portion 20 of the device assumes more a U-shaped appearance, as opposed to that depicted in FIG. 1. According to this variation, it may be more convenient to have a pad 22 formed as a continuous piece of material, as opposed to the separate portions 14 and 16 of FIG. 1.

To apply the inventive clip, a variety of applicators may be employed. Preferably, however, these will have the feel of traditional vascular clamps with ratcheted handles, allowing the surgeon to better control the amount of force applied to the clip, and thus the vessel, than a traditional hemostatic clip applier.

To remove the clip from the vessel, a hemostat or a pair of forceps can be used to grasp the clip and pull it off the vessel. By designing the metal/pad interface to break away at a predetermined force, the metal clip can be removed separately, allowing the pad to fall away from the vessel. For larger clips, the application device could be modified to allow for the clip to be seated on the applicator for removal.

In all embodiments, including those of FIGS. 1 and 2, the pad portions may be extended as indicated with the broken lines, to better facilitate grasping during removal. To further ensure positional stability, the pad surfaces facing one another, particularly those surfaces which extend beyond the malleable clip portion, may include means for engaging one another when compressed. For example, such means may include a pressure-sensitive adhesive or hook-and-loop type fastener arrangement.

Turning now to FIG. 3, there is shown a further variation of a clip according to the invention wherein, in contrast to the pad members forming a break-away releasable attachment to the metal clip portions of the device, the metal clip portion 30 and pad members 34 may include interlocking track features which, while preventing lateral and backward movements of the pads back toward the hinged section, do allow, preferably with the application of a pulling force, the pads to be removably slid off to facilitate straightforward removal. Toward this end, as in FIGS. 1 and 2, the pads may be extended by a distance shown with reference numeral 36, to provide a leader for a grasping tool as better understood with reference to FIG. 4. Although a true dovetail-type of engagement is depicted in FIG. 3, any other type of sliding engagement mechanism may alternatively be utilized.

Now making reference to FIG. 4, the clip 30 of FIG. 3 is now shown compressed over a vessel 40, thereby occluding the vessel. To remove this version of the clip, the practitioner need only grasp the crimped hinge section with a non-specialized tool 42, and the leader portions 36 with a second non-specialized tool 44, causing the two elements to separate from one another in opposite directions, thus facilitating straightforward removal.

Now turning to FIG. 5, there is shown yet a further alternative embodiment of the invention wherein a bent member 50 having a preferably smooth outer surface has been fitted with sleeves 52 and 54, again, which are preferably constructed of a compressible material such as silicone rubber. Again, the materials 52 and 54 are preferably provided with a leader portion 56, enabling the clip, once compressed over a vessel, to be removed in a manner similar to That depicted in FIG. 4.

Having thus described my invention, I claim:

1. A disposable clip for temporarily occluding a vessel, comprising:

a pair of substantially rigid, spaced-apart members, each having first and second ends, the first ends of the two members being joined through a malleable hinge, each member further including an inwardly oriented surface which faces the inwardly oriented surface of the other and outwardly oriented surfaces which face away from one another;

a layer of compressible material supported against the inwardly oriented surface of each member;

the distance between the inwardly oriented surfaces, including the layers of compressible material, being sufficient to a at least partially surround a vessel to be temporarily occluded therebetween, the clip having a first state wherein the vessel is at least partially surrounded, and a second state wherein an externally applied pressure is exerted upon the outwardly oriented surfaces, urging the members toward one another, thereby compressing and at least temporarily occluding the vessel between the layers of compressible material, with the malleable hinge maintaining the clip in its second state until removal; and means enabling the members and layers of compressible material to separate from one another through the application of an externally applied removal force.

2. The disposable clip of claim 1, wherein the members are generally parallel to one another in the first state.

3. The disposable clip of claim 1, wherein the members assume a V-shaped appearance in the first state.

4. The disposable clip of claim 1, wherein the means enabling the members and layers of compressible material to separate from one another includes a break-away bond therebetween.

5. The disposable clip of claim 1, wherein the means enabling the members and layers of compressible material to separate from one another includes a track feature between the inwardly oriented surfaces of each members and the layers of compressible material, enabling the members and layers of compressible material to be pulled in opposite directions to effectuate their separation.

\* \* \* \* \*